United States Patent [19]

Petrocci et al.

[11] 4,071,628
[45] Jan. 31, 1978

[54] SYNERGISTIC ANTIMICROBIAL MIXTURES

[75] Inventors: Alfonso N. Petrocci, Glen Rock; John J. Merianos, Jersey City, both of N.J.; Harold A. Green, Havertown, Pa.

[73] Assignee: Kewanee Industries, Bryn Mawr, Pa.

[21] Appl. No.: 761,319

[22] Filed: Jan. 21, 1977

[51] Int. Cl.$^2$ .................. A01N 9/00; A01N 9/20; A01N 9/22
[52] U.S. Cl. .................. 424/249; 424/316
[58] Field of Search .................. 424/316, 249

[56] References Cited

U.S. PATENT DOCUMENTS

| 2,867,562 | 1/1959 | Lamb | 424/316 |
| 2,921,881 | 1/1960 | Lamb | 424/316 |
| 2,990,266 | 6/1961 | Eden | 71/2.7 |
| 3,143,459 | 8/1964 | Marks et al. | 424/316 |
| 3,397,274 | 8/1968 | Clapp | 424/316 |
| 3,413,399 | 11/1968 | Wehner | 424/316 |

FOREIGN PATENT DOCUMENTS

| 1,148,706 | 5/1963 | Germany. |
| 1,812,054 | 6/1970 | Germany. |

OTHER PUBLICATIONS

Chem. Abst. 72, 11637(a) (1970), Burgand et al., "Fungides Treated --- foliage".

Primary Examiner—Albert T. Meyers
Assistant Examiner—D. W. Robinson
Attorney, Agent, or Firm—Arthur A. Jacobs

[57] ABSTRACT

Synergistic mixtures of a dodecylguanidine salt with the condensation product of formaldehyde and ethanolamine wherein the molar ratio of the formaldehyde and ethanolamine in the condensation product is about 1:1.

8 Claims, No Drawings

SYNERGISTIC ANTIMICROBIAL MIXTURES

This invention relates to synergistic mixtures of two antimicrobial agents. More specifically, this invention relates to synergistic mixtures of a dodecylguanidine salt with the condensation product of formaldehyde and ethanolamine, wherein the formaldehyde and ethanolamine are in a molar ratio of about 1:1.

The preferred guanidine derivative is dodecylguanidine acetate, while the condensation product appears to be N N' N"-tris-(2-hydroxyethyl)-hexahydrotriazine, the synthesis and properties of which are described in U.S. Pat. No. 2,990,266 and in German Pat. Nos. 1,148,706 and 1,812,054, all of which are incorporated herein by reference.

As disclosed in the aforesaid incorporated patents, the condensation product is prepared by reacting substantially equimolar portions of the ethanolamine and formaldehyde, at the reflux temperature of the reaction mixture, until the stoichiometric amount of water is formed. Optionally the reaction may be carried out in the presence of benzene, as disclosed in U.S. Pat. No. 2,990,266, although this is not necessary as disclosed in the German patents.

In accordance with the present invention, it has now been discovered that certain mixtures of the aforesaid compounds have antimicrobial properties which are far more potent and effective than the sum of the individual contributions of each component. Thus, as will be disclosed, the addition of a small quantity of one component to another results in a far more potent, and therefore more economical, mixture, which will achieve the same effect, but in lower concentrations, than could otherwise be expected.

The synergistic mixtures of the present invention have been found to be excellent microbiocides and preservatives which are effectively used in metal-working fluids, cutting oils, grinding fluids, lubricating fluids, cooling fluids, washing fluids, and the like. They may also be used in many other applications where antimicrobial or preservation properties are required.

The synergistic activity of mixtures of the two antimicrobials has been found to be particularly and uniquely effective against Gram-negative organisms, such as *Escherichia coli* and *Pseudomonas aeruginosa*, and against fungi such as *Aspergillis niger* and *Penicillium expansum*.

In the microbiological tests described below, growth inhibition tests were performed on pure dodecylguanidine acetate, which will hereinafter be referred to as "A" or "Compound A", on what is apparently pure N N' N"-tris-(2-hydroxyethyl)-hexahydrotriazine, which will hereinafter be referred to as "B" or "Compound B", and on mixtures of these two components in various ratios indicated by "B":"A".

The bacteriostatic and fungistatic activities of the pure compounds, and their mixtures, were determined as follows:

To test tubes holding 10 ml. of sterile nutrient broth, containing various concentrations of the compound or mixture to be tested, there was added 0.1 ml. of a 24-hour nutrient broth culture of bacteria in such manner that the contents had a concentration of 1–10 × $10^6$ organisms per ml.

The bacteria were incubated at 37° C for 72 hours, after which time the presence or absence of macroscopic bacterial growth was observed. The minimum concentration of either the pure compound or mixture which prevented macroscopic growth was designated the "Minimum Inhibitory Level" (MIL).

To test tubes holding 10 ml. of a sterile sabourad-dextrose broth, containing various concentrations of the compound or mixture to be tested, there was added 0.1 ml. of a saline suspension of fungi in such manner that the contents had a concentration of 0.5–1.0 × $10^6$ spores of fungi per ml.

The fungi were incubated at 25° C. for 14 days and the presence or absence of macroscopic growth at the end of 7 and 14 days, respectively, were observed. The minimum concentration of pure compound or mixture which prevented the macroscopic growth was designated as the MIL.

Table 1 lists the minimum inhibitory levels (MIL) in ppm. of pure "A" (dodecyclguanidine acetate), pure "B" (N N' N"-tris-(2-hydroxyethyl)-hexahydrotriazine), and a range of varous ratios of "B":"A", in which the relatively weaker "B" replaces the more potent "A". The minimum inhibitory levels for the pure compounds and mixtures are given for each of four organisms, two of which (*Escherichia coli* and *Pseudomonas aeruginosa*) are bacteria, and two of which (*Aspergillis niger* and *Penicilium expansum*) are fungi.

Tables 2, 3, 4 and 5 demonstrate the very effective synergistic interaction between "A" and "B" against each of the aforesaid organisms. Synergism was demonstrated by the same mathematical treatment of such data as used by Kull, Eisman, Sylwestrowicz and Mayer, described in "Applied Microbiology" 9, 538–541 (1946).

According to the aforementioned "Kull et al" method, the quantity of each component in the various mixtures is compared with the quantity of pure component that is required to reach the same end point or to produce the same microbiological effect as the mixture.

According to this mathematical treatment, synergism is demonstrated when:

$$(Q_A/Q_A^o) + (Q_B/Q_B^o) < 1$$

In this formula $Q_A^o$ and $Q_B^o$ are the minimum quantities of pure dodecylguanidine acetate and N N' N"-tris-(2-hydroxyethyl)-hexahydrotriazine respectively required to cause the complete inhibition of microbial growth of any species; and $Q_A$ and $Q_B$ are the respective quantities of these two components in the minimum inhibitory level of a mixture which also causes the complete inhibition of growth of the same microbial species.

Tables 2, 3, 4 and 5 show, conclusively, the dramatic synergism between these two antimicrobials in ratios "B":"A" of from 1:1 to 15:1.

These mixtures are inhibitorily active at concentrations shown in Table 1 and at any higher concentration, the only maximum limitation being such considerations as are related to economy which would make it impractical to use higher concentrations when lower concentrations are effective for the same purpose.

Table 1

| | Minimum Inhibitory Levels in ppm | | | |
|---|---|---|---|---|
| | BACTERIA | | FUNGI | |
| | E. Coli | P. Aeroginosa | A. Niger | P. Expansum |
| Pure "A" ($Q_A$) | 10 | 50 | 100 | 100 |
| Ratio "B":"A" | | | | |
| 1:1 | 10 | 25 | 150 | 150 |
| 3:1 | 10 | 90 | 75 | 75 |
| 5:1 | 10 | 90 | 75 | 75 |
| 7:1 | 10 | 150 | 250 | 250 |
| 9:1 | 75 | 175 | 250 | 250 |
| 11:1 | 75 | 200 | 250 | 250 |
| 13:1 | 75 | 250 | 250 | 250 |

Table 1-continued

| | Minimum Inhibitory Levels in ppm | | | |
|---|---|---|---|---|
| | BACTERIA | | FUNGI | |
| | E. Coli | P. Aeroginosa | A. Niger | P. Expansum |
| 15:1 | 75 | 400 | 250 | 250 |
| Pure "B" ($Q_B$) | 400 | 400 | 750 | 650 |

Table 2

| | E. Coli | | | | |
|---|---|---|---|---|---|
| | $Q_A = 10$ ppm | | | | |
| | $Q_B = 400$ ppm | | | | |
| Ratio "B":"A" | $\frac{Q_B}{\text{ppm}}$ | $\frac{Q_A}{\text{ppm}}$ | $\frac{Q_B}{Q_B}$ | $\frac{Q_A}{Q_A}$ | $\frac{Q_B}{Q_B} + \frac{Q_A}{Q_A}$ |
| 1:1 | 5 | 5 | .01 | .5 | .51 |
| 3:1 | 7.5 | 2.5 | .02 | .25 | .27 |
| 5:1 | 8:33 | 1:67 | .02 | .17 | .19 |
| 9:1 | 67.5 | 7.5 | .17 | .75 | .92 |
| 11:1 | 68.75 | 6.25 | .17 | .63 | .80 |
| 13:1 | 69.64 | 5.36 | .17 | .54 | .71 |
| 15:1 | 70.31 | 4.69 | .18 | .47 | .65 |

Table 3

| | P. Aeruginosa | | | | |
|---|---|---|---|---|---|
| | $Q_A = 50$ ppm | | | | |
| | $Q_B = 400$ ppm | | | | |
| Ratio "B":"A" | $\frac{Q_B}{\text{ppm}}$ | $\frac{Q_A}{\text{ppm}}$ | $\frac{Q_B}{Q_B}$ | $\frac{Q_A}{Q_A}$ | $\frac{Q_B}{Q_B} + \frac{Q_A}{Q_A}$ |
| 1:1 | 12.5 | 12.5 | .03 | .25 | .28 |
| 3:1 | 67.5 | 22.5 | .17 | .45 | .62 |
| 5:1 | 75 | 15 | .18 | .30 | .48 |
| 7:1 | 131.25 | 18.75 | .33 | .38 | .71 |
| 9:1 | 157.5 | 17.5 | .39 | .35 | .74 |
| 11:1 | 138.33 | 16.67 | .46 | .33 | .79 |
| 13:1 | 232.14 | 17.86 | .58 | .36 | .94 |
| 15:1 | 375 | 25 | .94 | .50 | 1.44 |

Table 4

| | A. Niger | | | | |
|---|---|---|---|---|---|
| | $Q_A = 100$ ppm | | | | |
| | $Q_B = 750$ ppm | | | | |
| Ratio "B":"A" | | | | | |
| 1:1 | 75 | 75 | .1 | .75 | .85 |
| 3:1 | 56.25 | 18.75 | .08 | .19 | .27 |
| 5:1 | 62.5 | 12.5 | .08 | .13 | .21 |
| 7:1 | 218.75 | 31.25 | .29 | .31 | .60 |
| 9:1 | 225 | 25 | .30 | .25 | .55 |
| 11:1 | 229.17 | 20.38 | .31 | .21 | .52 |
| 13:1 | 232.14 | 17.86 | .31 | .18 | .49 |
| 15:1 | 234.37 | 15.63 | .31 | .16 | .47 |

Table 5

| | P. Expansum | | | | |
|---|---|---|---|---|---|
| | $Q_A = 100$ ppm | | | | |
| | $Q_B = 650$ ppm | | | | |
| Ratio "B":"A" | $\frac{Q_B}{\text{ppm}}$ | $\frac{Q_A}{\text{ppm}}$ | $\frac{Q_B}{Q_B}$ | $\frac{Q_A}{Q_A}$ | $\frac{Q_B}{Q_B} + \frac{Q_A}{Q_A}$ |
| 1:1 | 75 | 75 | .12 | .75 | .87 |
| 3:1 | 56.25 | 18.75 | .09 | .19 | .28 |

Table 5-continued

| | P. Expansum | | | | |
|---|---|---|---|---|---|
| | $Q_A = 100$ ppm | | | | |
| | $Q_B = 650$ ppm | | | | |
| Ratio "B":"A" | $\frac{Q_B}{\text{ppm}}$ | $\frac{Q_A}{\text{ppm}}$ | $\frac{Q_B}{Q_B}$ | $\frac{Q_A}{Q_A}$ | $\frac{Q_B}{Q_B} + \frac{Q_A}{Q_A}$ |
| 5:1 | 62.5 | 12.5 | .10 | .13 | .23 |
| 7:1 | 218.75 | 31.25 | .34 | .31 | .65 |
| 9:1 | 225 | 25 | .34 | .25 | .59 |
| 11:1 | 229.17 | 20.38 | .35 | .21 | .56 |
| 13:1 | 232.14 | 17.86 | .36 | .18 | .54 |
| 15:1 | 234.37 | 15.63 | .36 | .16 | .52 |

In the above tables, Table 1 shows the minimum inhibitory amounts for each of the pure components and for eight illustrative mixtures, ranging from 1:1 to 15:1 ratios, for four different organisms.

Tables 2 to 5, in the first two columns of each table (each of these tables relating to a different one of the organisms shown in Table 1), shows the amount of each component in each mixture at the minimum inhibitory level shown in Table 1. For example, Table 1 indicates that for E. coli, a ratio of 1:1 has a minimum inhibitory level of 10 ppm. Table 2 indicates, therefore, that for E. coli, a 1:1 ratio requires 5 ppm of each component. At a ratio of 11:1 Table 1 indicates a minimum inhibitory level of 75 ppm. Table 2 shows, therefore, that at 11:1, against E. coli, the proportions are 68.75 and 6.25 ppm.

The invention claimed is:

1. A synergistic antimicrobial mixture consisting essentially of a dodecylguanidine salt and a condensation product formed by reacting substantially equimolar amounts of ethanolamine and formaldehyde at the reflux temperature of the reaction mixture until the stoichiometric amount of water is formed, said condensation product being present in the mixture in a ratio of about 1:1 to about 15:1 by weight relative to said dodecylguanidine salt.

2. The mixture of claim 1 wherein the dodecylguanidine salt is dodecylguanidine acetate.

3. A method of inhibiting the growth of bacteria and fungi which comprises applying to said bacteria and fungi an inhibitorily effective amount of synergistic antimicrobial mixture consisting essentially of a dodecylguanidine salt and a condensation product formed by reacting substantially equimolar amounts of ethanolamine and formaldehyde at the reflux temperature of the reaction mixture until the stoichiometric amount of water is formed, said condensation product being present in the mixture in a ratio of about 1:1 to about 15:1 by weight relative to said dodecylguanidine salt.

4. The method of claim 3 wherein the dodecylguanidine salt is dodecylguanidine acetate.

5. The method of claim 3 wherein the bacteria is Escherichia coli.

6. The method of claim 3 wherein the bacteria is Pseudomonas aeruginosa.

7. The method of claim 3 wherein the fungi is Aspergillis niger.

8. The method of claim 3 wherein the fungi is Penicilium expansum.

* * * * *